United States Patent [19]

Ogawa et al.

[11] Patent Number: 5,004,756

[45] Date of Patent: Apr. 2, 1991

[54] ANTI-CANCER ACTIVITY POTENTIATOR

[75] Inventors: Osamu Ogawa, Shiki; Ikuo Kishi, Ichikawa; Yoshiyuki Tahara, Tsurugashima; Masanori Sugita, Sakado, all of Japan

[73] Assignees: Lederle (Japan) Ltd.; Nisshin Flour Milling Co., Ltd., both of Tokyo, Japan

[21] Appl. No.: 390,875

[22] Filed: Aug. 8, 1989

[30] Foreign Application Priority Data

Aug. 11, 1988 [JP] Japan .................................. 198795

[51] Int. Cl.$^5$ ......................................... A61K 31/135
[52] U.S. Cl. .................................. 514/655; 514/937; 514/938
[58] Field of Search ....................... 514/937, 938, 655; 564/367, 370

[56] References Cited

PUBLICATIONS

Enhancement of Chemotherapeutic Effect on Lymph Node Metastasis by Anticancer Agents in Fat Emulsion, Takahashi et al., *Chemical Abstracts*, 88, 1978, #126307t.
Anticancer Agents Containing Epidermal Growth Factor, Pseudomones Exotoxin Conjugate and N–Solanesyl-N,N′-bis(3,4 dimethoxybenzyl) Ethylene Diamine, Akiyama et al.
*Chem. Abstracts*, 109, 1988, #79750v.
Overcoming Drug Resistance in Cancer Cells with Synthetic Isoprenoids, Yamaguchi et al., *JNCI* 76, p. 947, 1986.
Reversal of Multi Drug Resistance by Synthetic Isoprenoids in the KB Human Cancer Cell Line, Nakagawa et al., *Cancer Res.* 46, 4453, 1986.

*Primary Examiner*—Merrell C. Cashion, Jr.
*Assistant Examiner*—G. S. Kishore
*Attorney, Agent, or Firm*—Wenderoth, Lind & Ponack

[57] ABSTRACT

A pharmaceutical oil-in-water type microemulsion having an action of potentiating the activities of anti-cancer agents, said micro-emulsion comprises fine particles of a vegetable oil or a triglyceride of a medium-chain fatty acid having 8 to 12 carbon atoms containing 0.1 to 10% (w/v) of N-solanesyl-N,N′-bis(3,4-dimethoxybenzyl)ethylenediamine malate of formula (I) below,

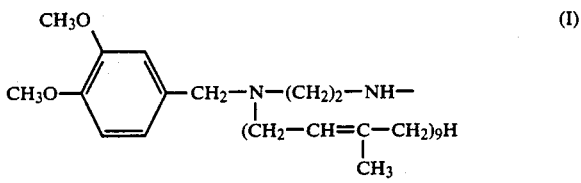

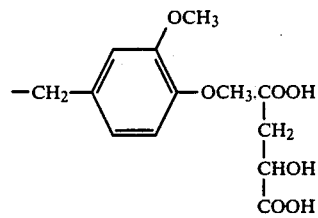

an aqueous medium, and, 0.05 to 25% (w/v) of a physiologically acceptable phospholipid for dispersing said fine particles in said aqueous medium.

8 Claims, No Drawings

ANTI-CANCER ACTIVITY POTENTIATOR

BACKGROUND OF THE INVENTION

1. Field of the Invention

This invention relates to a novel lipid emulsion having the activity of potentiating the anti-cancer activity of an anti-cancer agent, a method of potentiating the activities of anti-cancer agents by using it with the lipid emulsion, and to a method of treating cancer occurring in a warm-blooded animal by administering the novel lipid emulsion in combination with anti-cancer agents to the warm-blooded animal.

2. Description of the Prior Art

N-solanesyl-N,N'-bis(3,4-dimethoxybenzyl)ethylenediamine of the following formula (II)

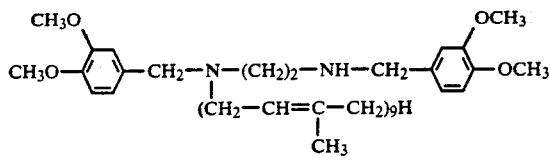

is a known compound.

The compound of formula (II) is described in the patent literature as one of a series of isoprenylamine derivatives having antiviral and antitumoral activities (see, for example, Japanese Laid-Open Patent Publication No. 192339/1982 and its corresponding U.S. Pat. Nos. 4645862, 4658063, 4700002 and 4323008).

In recent years various carcinostats and anti-cancer agents against solid tumors such as lung cancer, stomach cancer, breast cancer, bladder cancer and testicular tumor or tumors in the hematopoietic organs such as leukemia and malignant lymphoma have been developed, but no drug has yet come out which can completely cure or prevent these malignant tumors. For example, cyclophosphamide (CPA), melphalan (MPL), nimustine (ACNU), carboquone (CQ), vincristine (VCR), vinblastine (VLB), vindesine (VDS), bleomycin (BLM), 5-fluorouracil (5-FU), adriamycin (ADM), cisplatin (CDDP), actinomycin D (ACD), methotrexate (MTX), aclarubicin (ACR), toyomycin (TM), neocartinostatin (NCS), and ifosfamide (Ifos) have been used heretofore therapeutically as anti-cancer agents (the parenthesized letters show abbreviated designations which may sometimes be used hereinafter). These drugs are used selectively and specifically in various areas because of their inherent anti-cancer spectra. For example, adriamycin (ADM) has a broader anti-cancer spectrum than other drugs, and is used against breast cancer, bladder cancer, lung cancer, testicular tumor, malignant lymphoma, and acute leukemia. However, the efficacy of ADM on these diseases is limited, and cancer cells showing resistance to ADM have appeared. A further cumbersome and complex problem is that other drugs do not show an anti-cancer action on these ADM-resistant cancer cells.

The appearance of drug-resistant tumor cells also becomes a problem with drugs other than ADM.

Recently, searching for compounds effective on these drug-resistant tumor cells was considered, and it has so far been found that when N-solanesyl-N,N'-bis(3,4-dimethoxybenzyl)ethylenediamine itself or its hydrochloride is combined with ADM, the pharmacological efficacy of ADM can be potentiated, particularly against ADM-resistant tumor cells. This finding was applied for a patent (Japanese Laid-Open Patent Publication No. 200913/1986).

The present inventors further made investigations in order to overcome the problem of the drug-resistance of tumor cells, and determined that an acid salt, especially a malate, of N-solanesyl-N,N'-bis(3,4-dimethoxybenzyl)ethylenediamine of formula (II) above has excellent anti-cancer activity as compared with the compound (II) and it hydrochloride and can potentiate the pharmacological efficacy of not only adriamycin but also other anti-cancer agents, particularly the anti-cancer activity of these compounds on drug-resistant tumor cells, and that this activity has some degree of specificity.

The present inventors have further found that when the malate of compound (II) is administered in a form incorporated in lipid microspheres by applying the drug delivery system (DDS), the lipid microspheres are transferred selectively to tumor cells, and the incorporated malate exhibits its effect in situ, and that this offers an effective therapeutic method.

SUMMARY OF THE INVENTION

This invention relates to a lipid emulsion containing N-solanesyl-N,N'-bis(3,4-dimethoxybenzyl)ethylenediamine malate represented by the following formula (I)

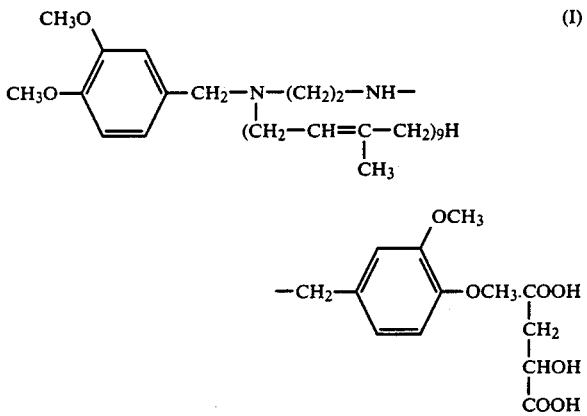

More specifically, this invention relates to a lipid emulsion having the action of potentiating the activities of anti-cancer agents. By using the lipid emulsion in combination with anti-cancer agents, the activities of the anti-cancer agents can be potentiated.

According to this invention, there is provided a pharmaceutical oil-in-water type micro-emulsion having the action of potentiating the activities of anti-cancer agents, said emulsion comprising fine particles of a vegetable oil or a triglyceride of a medium-chain fatty acid having 8 to 12 carbon atoms containing 0.1 to 10% w/v) of N-solanesyl-N,N'-bis(3,4-dimethoxybenzyl)ethylenediamine malate of formula (I) above, an aqueous medium, and 0.05 to 25% (w/v) of a physiologically acceptable phospholipid for dispersing said fine particles in said aqueous medium.

In a preferred embodiment, the vegetable oil is pharmaceutically acceptable soybean oil.

In another preferred embodiment, the physiologically acceptable phospholipid is a purified vegetable oil phospholipid, preferably purified soybean oil phospholipid.

Preferably, an isotonizing agent is added to the lipid emulsion of the invention. Examples of the isotonizing agent are glycerol, sugar alcohols, monosaccharides, disaccharides, and amino acids. Thus, in a further preferred embodiment, there is provided a microemulsion consisting essentially of 5 to 50% (w/v) of fine particles of a vegetable oil or a triglyceride of a medium-chain fatty acid having 8 to 12 carbon atoms containing 0.1 to 10% (w/v) of N-solanesyl-N,N'-bis(3,4-dimethoxybenzyl)ethylenediamine malate, 0.05 to 25% (w/v) of physiologically acceptable phospholipid, an isotonizing agent selected from the group consisting of glycerol, sugar alcohols, monosaccharides, disaccharides and amino acids in an amount sufficient to isotonize the emulsion, and water.

In still another preferred embodiment, there is provided a pharmaceutical oil-in-water micro-emulsion consisting essentially of 5 to 30% (w/v) of fine particles of soybean oil having dissolved therein 0.3 to 3% (w/v) of N-solanesyl-N,N'-bis(3,4-dimethoxybenzyl)ethylenediamine malate of formula (I), 0.5 to 25% (w/v) of a purified soybean oil phospholipid, and the remainder being water.

According to a second aspect, the present invention provides a method of potentiating the activities of anti-cancer agents by administering the anti-cancer agents in combination with the lipid emulsion of the invention.

According to a third aspect of the invention, there is provided a method of effectively treating cancer occurring in a warm-blooded animal, which comprises administering an anti-cancer agent in combination with the lipid emulsion of the invention to the animal.

In a preferred embodiment, the lipid emulsion of the invention is intravenously administered.

In another preferred embodiment, the lipid emulsion is administered within 24 hours before the administration of the anti-cancer agent.

In an additional preferred embodiment, the lipid emulsion is administered for the first time within 24 hours before the administration of the anti-cancer agent, and thereafter, the lipid emulsion is further administered nearly simultaneously with, or several hours before, the administration of the anti-cancer agent. If desired, this course of administration is thereafter repeated.

The present invention is unique in that the lipid emulsion preparation exhibits an excellent effect at a low dose of the malate of formula (I), and in that when used in combination with an anti-cancer agent, the lipid emulsion preparation markedly potentiates the activities of the anti-cancer agents.

DETAILED DESCRIPTION OF THE INVENTION

N-solanesyl-N,N'-bis(3,4-dimethoxybenzyl)ethylenediamine of formula (II), one free base of the malate of formula (I) provided by this invention, is a colorless transparent oily substance, but the malate of formula (I) is a colorless to pale yellow crystal having a melting point of 42° to 44°. The malate can be obtained, for example, by the following method. N-solanesyl-N,N'-bis-(3,4-dimethoxybenzyl)ethylenediamine is dissolved in a suitable organic solvent, preferably an alcohol such as methanol, ethanol or propanol or an ether such as diethyl ether, tetrahydrofuran or dioxane. A solution of malic acid in an amount of 1.0 to 1.5 moles per mole of the compound of formula (II) is added to the above solution. The mixed solution is heated, and then the solvents are evaporated. The residue was washed with an ether solvent, and recrystallized to give the desired malate.

The malate of formula (I) has been found to be very easy to handle in view of the fact that the compound of formula (II) or its hydrochloride is a resinous ultraviscous compound. The malate of formula (I) itself is characterized not only by having anti-cancer activity but also by markedly potentiating the activities of other anti-cancer agents when used with the other anti-cancer agents. The invention is especially excellent in that when the malate of formula (I) is formed into a lipid emulsion, it is incorporated in lipid microspheres of the emulsion. These lipid microspheres are transferred to tumor cells; and in that in situ, the malate of formula (I) incorporated in the microspheres potentiates the activities of the anti-cancer agents, thus providing an effective therapeutic effect.

Various anti-cancer agents heretofore used clinically can be potentiated in activity. Specific examples include adriamycin, actinomycin-D, mitomycin C, bleomycin, 5-fluorouracil, peplomycin and cisplatin. The lipid emulsion may be said to be unique in that it can exhibit an excellent effect on tumor cells which show resistance to these drugs.

In the present invention, the lipid emulsion containing the malate of formula (I) is administered in combination with other anti-cancer agents. Its dose may vary depending upon the method of administration and a disease to be treated. Generally, its amount as the malate of formula (I) may be 1.0 mg to 2,000 mg/day. The suitable amount is 4 mg to about 1,000 mg/day. In the administration of the lipid emulsion of the invention together with the other anti-cancer agents for the purpose of potentiating the activities of the other anti-cancer agents, the dose of the emulsion of the invention differs depending upon the type of the other anti-cancer agents. Generally, the doses of the other anti-cancer agents are those conventionally used, and the dose of the malate of formula (I) is selected from those which potentiate the activities of the other anti-cancer agents. In actual administration, the lipid emulsion is in a stable dosage form, and this is unique in view of the fact that the compound (II) itself or its hydrochloride cannot be formed into a lipid emulsion.

To secure fine particles of 1 micron or below in size which can actually be administered as a lipid emulsion, the particles should have a charge within the range of +20 mV to +50 mV. It has been found however that compound (II) itself or its hydrochloride does not have a particle charge within this range, but particle aggregation occurs.

Accordingly, to obtain a lipid emulsion of N-solanesyl-N,N'-bis(3,4-dimethoxybenzyl)ethylenediamine of formula (II) which exhibits the inherent pharmacological efficacy of the compound (II) must be converted to its malate. The lipid emulsion of this invention may be said to be unique in respect of this feature.

The pharmaceutical micro-emulsion of this invention is prepared by introducing the compound of formula (I) into particles of an oil or fat used in the preparation of ordinary lipid emulsions. For example, it can be easily prepared by dissolving the compound of formula (I) in fine particles of the oil or fat, and dispersing the fine particles in water using an emulsifier to form an oil-in-water emulsion.

The oil or fat which can be used in preparing the pharmaceutical micro-emulsion of this invention includes any pharmaceutically acceptable oils and fats which are normally used. Specific examples include vegetable oils such as soybean oil, cottonseed oil, rapeseed oil and safflower oil; triglycerides of medium-chain fatty acids having 8 to 12 carbon atoms (such as caprylic acid, capric acid and lauric acid), normally abbreviated as MCT; and mono- or di-glycerides of fatty acids having 6 to 18 carbon atoms (such as caproic acid, capric acid, myristic acid, palmitic acid, linoleic acid and stearic acid). They may be used either singly or in combination. Among them, vegetable oils and Panacet 810 (MCT mixture, a product of Nippon Oils and Fats Co., Ltd.) are preferably used, and pharmaceutically acceptable soybean oil fitting the standards of medicines stipulated in Japanese Pharmacopoeia is most preferred. The amount of such an oil or fat is not strictly limited, and can be varied widely depending upon the type or amount of the pharmacologically effective compound of formula (I) and/or the other ingredients. Generally, it is 1 to 50% (w/v), preferably 3 to 30% (w/v), more preferably 5 to 20% (w/v).

Unless otherwise stated, all percentages "% (w/v)" used to denote the contents or amounts used of the ingredients of the pharmaceutical micro-emulsion in the present specification and the appended claims mean parts by weight per 100 parts by volume of the final pharmaceutical micro-emulsion.

The emulsifier used to disperse the fine particles of the oil or fat stably in an aqueous medium may be at least one compound selected from physiologically acceptable phospholipids and nonionic surface-active agents, preferably the physiologically acceptable phospholipids. Examples of the physiologically acceptable phospholipids include yolk phospholipid, vegetable oil phosphplipids such as soybean phospholipid, and phosphatidyl choline. Examples of the nonionic surface-active agents include polyoxyalkylene copolymers (for example, polyoxyethylene-polyoxypropylene copolymers having an average molecular weight of 1,000 to 20,000), and hydrogenated castor oil polyoxyalkylene derivatives [such as hydrogenated castor oil polyoxyethylene-(40)-ether and hydrogenated castor oil polyoxyethylene-(20)-ether]. These emulsifiers can be used either singly or in combination. Preferably, the emulsifiers used in this invention generally have an HLB of 6 to 15, preferably 10 to 14. Among the above emulsifiers, yolk phospholipid and vegetable phospholipids such as soybean phospholipid are preferred. The vegetable oil phospholipids, particularly purified soybean phospholipid, are most suitable because they have a better emulsifying power and can form more uniform, finer and more stable phospholipid particles than the yolk phospholipid. Desirably, the vegetable oil phospholipids are purified to such an extent that the phosphatidyl choline content reaches at least 50% by weight, preferably at least 80% by weight. The soybean oil phospholipid so purified may have an iodine value of generally 30 to 50, preferably about 40.

The emulsifier is used in an amount sufficient to disperse the oil or fat particles containing the N-solanesyl-N,N'-bis(3,4-dimethoxybenzyl)ethylenediamine malate in an aqueous medium and maintain them stably in it.

Depending upon the type of the emulsifier, its amount is generally 0.05 to 25% (w/v), preferably 0.2 to 6% (w/v), more preferably 0.6 to 2.4% (w/v). On the basis of the oil or fat, the suitable amount of the emulsifier is 6 to 24 parts by weight, especially 6 to 15 parts by weight, per 100 parts by weight of the oil or fat.

In the micro-emulsion of the present invention, a moderate amount of distilled water or deionized water may be used as the aqueous dispersion medium. If required, a small amount of a pharmaceutically acceptable water-miscible organic solvent such as ethanol may be incorporated.

As required, an isotonizing agent and other additives such as an emulsification aid and a stabilizer may further be incorporated in the micro-emulsion of the present invention.

Examples of the isotonizing agent include glycerol, sugar alcohols such as sorbitol and xylitol; monosaccharides such as glycose and fructose; disaccharides such as maltose; and amino acids such as L-alanine, L-valine and glycine. Of these, glycerol is especially suitable.

The isotonizing agent is added to adjust the osmotic pressure of the micro-emulsion to a value nearly equal to that of a body fluid. The amount of the isotonizing agent is such that its final concentration in the micro-emulsion is 0.1 to 0.5 mole/liter, preferably 0.25 to 0.35 mole/liter.

Examples of the emulsifying aid that can be incorporated include fatty acids having 10 to 20 carbon atoms (such as stearic acid, palmitic acid, linoleic acid and linolenic acid) and salts thereof (such as sodium and potassium salts), phosphatidyl ethanolamine, phosphatidyl serine and stearylamine. It may be used generally in an amount of up to 0.4% (w/v), preferably 0.01 to 0.2% (w/v). In particular, the fatty acid or its salt can be advantageously used in an amount of 0.01 to 0.1% (w/v), and phosphatidyl ethanolamine, phosphatidyl serine and stearylamine may be advantageously used in an amount of 0.05 to 0.3% (w/v), especially 0.1 to 0.2% (w/v).

Cholesterol or tocopherol, for example, may be used as a stabilizer. Conveniently, cholesterol may be used generally in an amount of up to 1.2% (w/v), preferably 0.2 to 0.4% (w/v), and tocopherol may conveniently be used in an amount of up to 2.5% (w/v), preferably 0.2 to 0.8% (w/v).

Albumin, its fatty acid amide derivatives, and polysaccharides or their fatty acid ester derivatives may also be used as the stabilizer. From the standpoint of antigenicity, albumin is desirably one derived from a human when preparing a pharmaceutical micro-emulsion for humans. The fatty acid amide derivatives thereof may, for example, be compounds obtained by amidating 5 to 40% of the entire amino groups present in albumin with fatty acids having 14 to 18 carbon atoms (such as palmitic acid and stearic acid). Examples of the polysaccharides include dextran, pullulan and hydroxyethyl starch. The fatty acid ester derivatives of these polysaccharides may be compounds obtained by, for example, esterifying 5 to 40% of the entire hydroxyl groups present in the polysaccharides with fatty acids having 14 to 18 carbon atoms such as palmitic acid and stearic acid. The stabilizer may be added generally in an amount of 0.02 to 5% (w/v), preferably 0.2 to 2.5% (w/v).

The micro-emulsion of this invention may be prepared by using emulsifying methods known per se. Ordinary homogenizers may be used as an emulsifying machine. To prepare a stable lipid micro-emulsion, it is convenient to use two types of homogenizer. Specifically, the micro-emulsion of this invention may be prepared by dissolving an effective amount of the 4-biphenylylacetic acid ester in the oil or fat such as pharmaceutically acceptable soybean oil optionally under heat, adding a predetermined amount of an emulsifier such as refined soybean phospholipid and as required an isotonizing agent and other additives such as an emulsification aid or a stabilizer, stirring the mixture under heat to make a uniform mixture, adding water, and treating the mixture in a homogenizer to prepare a crude emulsion of the oil-in-water type, and thereafter, homogenizing the crude emulsion by a pressurized homogenizer such as Gaulin high-energy homogenizer. The stabilizer and the isotonizing agent may be added to the resulting micro-emulsion.

Desirably, the above emulsifying operation is carried out generally until the dispersed oil or fat particles in the resulting emulsion have a mean particle diameter of not more than about 1 micron, preferably not more than 0.3 micron, more preferably 0.1 to 0.15 micron.

N-Solanesyl-N,N'-bis(3,4-dimethoxybenzyl)ethylenediamine malate of formula (I) as a pharmacologically active ingredient is conveniently used so that its concentration generally becomes 0.1 to 10% (w/v), preferably 0.3 to 3% (w/v), more preferably 1 to 3% (w/v).

As required, the micro-emulsion of this invention so prepared may be lyophilized. The powder obtained by lyophilization can be converted back to the original micro-emulsion when it is dissolved in water. It should be understood that the term "micro-emulsion", as used in the present application, also denotes such a lyophilized form of the micro-emulsion.

Thus, according to one preferred embodiment of this invention, there is provided a pharmaceutical oil-in-water type micro-emulsion consisting essentially of 5 to 50% (w/v) of fine particles of a vegetable oil or a triglyceride of a medium-chain fatty acid having 8 to 12 carbon atoms containing 0.1 to 10% (w/v) of N-solanesyl-N,N'-bis(3,4-dimethoxybenzyl)ethylenediamine malate, 0.05 to 25% (w/v) of a physiologically acceptable phospholipid, an isotonizing agent selected from the group consisting of glycerol, sugar alcohols, monosaccharides, disaccharides and amino acids in an amount sufficient to isotonize the emulsion, and water.

According to a more preferred embodiment of this invention, there is provided a pharmaceutical oil-in-water type emulsion consisting essentially of 5 to 30% (w/v) of fine particles of soybean oil having dissolved therein 0.3 to 3% (w/v) of N-solanesyl-N,N'-bis(3,4-dimethoxybenzyl)ethylenediamine malate, 0.5 to 25% (w/v) of a purified soybean oil phospholipid, 1 to 5% (w/v) of glycerol, and the remainder being water.

The lipid emulsion provided by this invention containing the compound of formula (I) is parenterally administered by injection or the like. Preferably, it is administered intravenously. When parenterally administered, the lipid emulsion has very good migrability to tumor cells (uptake into the tumor cells), and consequently, can strongly potentiate the activities of other anti-cancer agents.

In the method of potentiating the activities of other anti-cancer agents by using the lipid emulsion provided by this invention in combination with the other anti-cancer agents and the method of treating cancer occurring in a warm-blooded animal by administering the lipid emulsion of the invention to the warm-blooded animal together with the other anti-cancer agents, the actual administration schedule of the lipid emulsion of the invention is preferably by the following specific method.

In one embodiment, the lipid emulsion of the invention is administered together with the other anti-cancer agents. In another embodiment, the lipid emulsion of this invention is administered for the first time within 24 hours before the administration of anti-cancer agents, and then the lipid emulsion of the invention is further administered simultaneously with, or several hours before, the administration of the anti-cancer agents, and this administration course is continuously or intermittently repeated. By this administering method, the activities of the other anti-cancer agents used in combination are markedly potentiated, and the therapeutic effect can be effectively exhibited.

Accordingly, the lipid emulsion of this invention contributes greatly to cancer therapy.

The pharmacological activities of N-solanesyl-N,N'-bis(3,4-dimethoxybenzyl)ethylenediamine and a lipid emulsion containing the malate will now be illustrated specifically.

[A] PHARMACOLOGICAL TESTS

A-I: Anti-cancer activity and potentiation activity in vitro

Part 1

Procedure

Sensitive cell line V79/S and ADM-resistant cell line V79/ADM of the Chinese hamster were used, and sensitive cell line PLC/S and cholchicin-resistant cell line PLC/Col, as human hepatoma cells.

The sensitive cell lines (400 cells) or the resistant cell lines (600 cells) were each incubated for 24 hours in 10 ml of Eagle's MEM medium containing 10% bovine serum. Each of the drugs indicated in Table 1 below was dissolved in ethanol, and 50 microliters of the resulting solution was added to the medium. The incubation was further carried out for 9 days. The concentration of the drug which inhibits 50% of the colony formation (proliferation) of the tumor cells was calculated.

V79/S and V79/ADM were tested by using all of the drugs described above, but PLC/S and PLC/Col were tested by using only the malate of formula (I), adriamycin and peplomycin.

Results

The concentrations (micrograms/ml) required to inhibit 50% of the proliferation of the tumor cells, expressed by $IC_{50}$, are shown in Table 1.

TABLE 1

| Drug | Cell line $IC_{50}$ (μg/ml) | | | |
| --- | --- | --- | --- | --- |
| | V79/S | V79/ADM | PLC/S | PLC/Col |
| Compound (I) | 11.5 | 3.0 | 6.8 | 1.7 |
| ADM | 0.057 | 8.8 | 0.005 | 0.08 |
| ACR | 0.037 | 0.27 | — | — |
| ACD | 0.017 | 0.28 | — | — |
| CDDP | 0.37 | 0.32 | — | — |
| MTX | 0.017 | 0.0078 | — | — |
| Mitoxantrone | 0.019 | 0.36 | — | — |

TABLE 1-continued

| Drug | Cell line IC$_{50}$ (μg/ml) | | | |
|---|---|---|---|---|
| | V79/S | V79/ADM | PLC/S | PLC/Col |
| PEP | 1.95 | 0.48 | 0.24 | 0.19 |

It is clear from the results given in Table 1 that the malate of formula (I) itself had some degree of tumor growth inhibition activity (anti-cancer activity), and inhibited proliferation of ADM-resistant Chinese hamster cells (V79/ADM) or colchicin-resistant human hepatoma cells (PLC/Col) in concentrations required to inhibit growth of their sensitive cell lines; and therefore that the malate of formula (I) showed clear tumor growth inhibition (anti-cancer) activity on drug-resistant tumor cells and drug-resistance overcoming activity.

In contrast, the adriamycin (ADM) clinically used showed a marked reduction in its anti-cancer activity on ADM-resistant tumor cells. ACR and ACD which are other carcinostats or anti-cancer agents, and mitoxantrone recently marketed for their appreciable anti-cancer activity on acute leukemia, acute lymphoma and breast cancer have larger IC$_{50}$ values on the proliferation of drug-resistant tumor cells V79/ADM than those on the sensitive cell lines. Hence, the resistances to these drugs were not overcome.

It will be understood that the malate of formula (I) is excellent.

Part 2

Procedure

Lung adenocarcinoma, lung squamous cell carcinoma, osteosarcoma and ovarian carcinoma were selected as clinically isolated human cancer cells, and the anti-tumor activities of various drugs were examined. Specifically, various tumor tissues were individually cut to thin pieces by a razor, and by washing in saline by using a 1 mm mesh, the connective tissues were removed. The resulting solution was centrifuged at 1000 rpm for 1 minute to remove necrotizing substances. Washing with saline gave tumor cells.

The tumor cells obtained as above (about 10 g) were put in 0.4 ml of a culture solution (RPMI 1640 plus 10% calf serum), and each of the drugs in the concentration shown in Table 2 was added. They were incubated at 37° for 4 to 8 hours. Thereafter, pumping was carried out to disperse the tissue pieces. Then, centrifugation at 1000 rpm for 5 minutes, cell coating and Giemsa staining were performed. The anti-tumor activity of each drug was examined on the basis of observation of the morphological changes of the tumor cells under a microscope.

The experiment was conducted on two examples of each tumor cells (total 8 examples). The malate of formula (I) was used in a concentration of 3 micrograms/ml for 3 examples out of 8, and 30 micrograms/ml on 5 examples.

Results

The anti-tumor activities on the tumor cells were examined by using the effective dose of the drugs in vivo. The results with those examples which were rated as "significant" by the Fisher's significance test are given in Table 2.

TABLE 2

| Drug | Drug concentration (μg/ml) | Efficacy ratio (*) |
|---|---|---|
| Compound (I) | 3 or 30 | 5/8 |
| CDDP | 0.5 | 4/8 |
| CPM | 10 | 3/8 |
| ADM | 0.3 | 3/8 |
| ACNU | 2.0 | 3/8 |
| VLB | 0.1 | 3/8 |
| BLM | 1.0 | 2/8 |
| VCR | 0.1 | 2/8 |
| ACR | 0.2 | 2/8 |
| MPL | 0.5 | 1/8 |
| CQ | 0.1 | 1/8 |
| 5-FU | 10 | 1/8 |
| MTX | 3.0 | 1/8 |
| MMC | 0.2 | 0/8 |
| VDS | 0.5 | 0/8 |
| ACD | 0.01 | 0/8 |

(*)Rated as "significant" by the Fisher's significance test.

As is clear from the examples given in Table 2, the malate of formula (I) in accordance with this invention was found to have anti-tumor activity on various tumor cells.

A-II: Anti-cancer activity and potentiation activity in vivo

Part I

Procedure

Three to eight male BDF$_1$ mice having a body weight of 20±3 g were used, and B16 melanoma cells were selected as tumor cells. The melanoma cells were homogenized, and the homogenate was transplanted subcutaneously to the mice in an amount of 0.5 ml/mouse. After 7 days, the malate of formula (I) in accordance with this invention and an anti-cancer agent, neocartinostatin (NCS), were intraperitoneally administered either singly or in combination three times every 4 days in a dose of 5 mg/kg and 0.45 mg/kg for each time. The life prolonging rate of the mice was determined by the treated group/non-treated control group (T/C %).

Results

The T/C (%) values are tabulated in Table 3.

TABLE 3

| Drug | T/C (%)* |
|---|---|
| Control | 100 |
| Compound (I) | 165 |
| NCS | 135 |
| Compound (I) + NCS | 129 |

*Comparison at M.S.T. (medium survival time)

As is clear from the results given in Table 3, the group to which the malate of formula (I) was administered showed a particularly good life prolongation effect as compared with the non-treated control group, and was also found to have a significant effect over the group to which NCS alone was administered. The group to which these drugs were administered in combination showed no difference in life prolongation rate as compared with the groups to which the drugs were administered alone. In this test, anti-cancer activity potentiating action was not clearly seen.

Part 2

Procedure

Male BDF$_1$ mice having a body weight of 20±2 g (6 per group) were used, and as tumor cells, Lewis lung cancer cells were transplanted under the skin of the side abdomen of each of the mice at a rate of 10$^5$ cells. Seven days later, a lipid emulsion containing the malate of formula (I) (the lipid emulsion of Example 2) and ADM as an anti-cancer agent were intravenously administered in the doses shown in Table 4 below. The life prolongation rate of the mice in each group was determined by the treated group/non-treated control group (T/C %).

Results

The T/C (%) values are shown in Table 4.

TABLE 4

| Drug | Dose (mg/kg) | T/C (%)[1] |
|---|---|---|
| Control | | 100 |
| Lipid emulsion[2] | 2.5 | 205 |
| of Example 2 | 5.0 | 179 |
| | 10 | 103 |
| | 20 | 203 |
| ADM | 1.25 | 218 |
| | 2.5 | 173 |
| | 5.0 | 241 |

[1]Comparison at M.S.I.
[2]Calculated as the malate of formula (I)

It is seen from the results shown in Table 4 that the lipid emulsion containing the malate of formula (I) shows a marked life prolongation effect and excellent anti-cancer activity.

Procedure

Male BDF$_1$ mice having a body weight of 20±2 g, 6 per group, were used. P388 mouse leukemia cells (one week after transplantation) as tumor cells were washed with 0.9% saline and suspended in saline so that the number of the cells reached $5 \times 10^6$/m. The suspension was intraperitoneally administered to the mice at a rate of 0.2 ml ($10^6$ cells) per mouse.

Twenty-four hours after the transplantation of tumor cells, the malate of formula (I) and cyclophosphamide (COPA) were successively administered intraperitoneally once to the mice, and the life prolongation rate of the mice in each group was determined.

The malate of formula (I) was used after suspending it and Tween 80 at a ratio of 1:5 to saline, and this suspension was diluted with a solution of Tween 80 in the same concentration. CPA, on the other hand, was used as a solution in saline.

CPA (50 mg/kg and 100 mg/kg) and the malate of formula (I) (10 mg/kg and 20 mg/kg) were administered singly or in combination, and the life prolongation rate was determined. The life prolongation rate shows the rate of the treated group to the control group into which P288 mouse leukemia cells were transplanted (T/C %), and the rate of the group to which CPA and the malate were administered to the group to which CPA alone was administered (T/C %). The results are summarized in Table 5. The number of surviving mice determined 30 days later was also shown in Table 5.

TABLE 5

| Drug (dose) | MST[1] | T/C[2] (%) | Number of[3] surviving animals |
|---|---|---|---|
| Control group having P388 cells transplanted therein | 10.1 [9-11] | 100 — | 0/6 |
| CPA (50 mg/kg) | 20.3 [19-22] | 201 (100) | 0/6 |
| + Compound (I) | | | |
| (5 mg/kg) | 21.3 [19-29] | 211 (105) | 0/6 |
| (10 mg/kg) | 22.0 [20-23] | 218 (108) | 0/6 |
| (20 mg/kg) | 22.3 [19-23] | 221 (110) | 0/6 |
| (40 mg/kg) | 9.3 [8-26] | 92 (46) | 0/6 |
| CPA (100 mg/kg) | 24.0 [21-30] | 238 (100) | 1/6 |
| + Compound (I) | | | |
| (5 mg/kg) | 29.0 [22-30] | 287 (121) | 0/6 |
| (10 mg/kg) | >31.0 [27->30] | >341 (>143) | 5/6 |
| (20 mg/kg) | 12.0 [4-30] | 119 (50) | 1/6 |
| (40 mg/kg) | 9.3 [3-11] | 92 (39) | 0/6 |

[1]MST: Medium Survival Time
[2]The parenthesized figures show percentages based on the group to which CPA alone was administered.
[3]Number of animals which survived for 30 days.

The above results show that the malate of formula (I) in accordance with this invention at low concentrations markedly potentiated the anti-cancer activity of CPA, and particularly in the group to which CPA was administered in a dose of 100 mg/kg, the combined use of 10 mg/kg of the malate exhibited an excellent potentiating efficacy.

A-III Anti-cancer activity potentiating action

Procedure

The anti-cancer activity potentiating action of the malate of formula (I) was examined using Chinese hamster cells (sensitive cell line V79/S and ADM-resistant cell line V79/ADM), human hepatoma cells (sensitive cell line PLC/S and colchicin-resistant cell line PLC/Col) and mouse leukemia cells (sensitive cell line L5178Y/S) and aclarubicin-resistant cell line L5178Y/ACR).

Of these tumor cells, the sensitive cells (400 cells) and the resistant cells (600 cells) were each incubated in 10 ml of Eagle's MEM medium containing 10% bovine serum for 24 hours, and then each of the test drugs indicated in Table 6 was added. Thereafter, the incubation was carried out for 9 days. The concentration (IC$_{50}$: micrograms/ml) of the test drug required to inhibit 50% of the colony formation (proliferation) of the tumor cells was calculated.

Specifically, the experiment was carried out by using the following anti-cancer agents.

(A) Chinese hamster V79 cells

As anti-cancer agents, there were used adriamycin (ADM), aclarubicin (ACR), actinomycin D (ACD), 5-fluorouracil (5-FU), cytarabin (Ara-C), cisplatin (CDDP), methotrexate (MTX), mitomycin C (MMC), nimustine (ACNU), mitoxantrone, etoposide (VP-10), vincristine (VCR), bleomycin (BLM) and peplomycin (PEP). For the sensitive cells, the anti-cancer agents were used in combination with 10 micrograms/ml of the malate of formula (I), and for the resistant cells, the anti-cancer agents were used in combination with the malate of formula (I) 3 micrograms/ml, 5 micrograms/ml, and 10 micrograms/ ml.

(B) Human hepatoma cells

As anti-cancer agents, adriamycin (ADM) and peplomycin (PEP) were used in combination with the malate of formula (I) (5 micrograms/ml).

(C) Mouse leukemia cells

Adriamycin (ADM) and aclarubicin (ACR) as anti-cancer agents were used in combination with 20 micrograms/ml of the malate of formula (I).

Results

The results are summarized in Tables 6 and 7.

TABLE 6

| | Cell line | | | | | | |
|---|---|---|---|---|---|---|---|
| | V79/S (parent cells) | | | V79/ADM (resistant cells) | | | |
| Anti-cancer agent | Anti-cancer agent alone | Compound [in combination with compound (I)] 10 μg/ml | Potentiation activity (times) | Anti-cancer agent alone | Combination with compound (I) | | Potentiation activity (times) |
| | | | | | 3 μg/ml | 5 μg/ml | 10 μg/ml | |
| Compound (I) | 11.5 | — | — | 3.0 | — | — | — | — |
| ADM | 0.057 | 0.008 | 7.1 | 8.8 | — | — | 0.25 | 35.2 |
| ACR | 0.037 | 0.027 | 1.37 | 0.27 | — | — | 0.024 | 11.3 |
| ACD | 0.017 | 0.0032 | 5.3 | 0.28 | — | — | 0.0063 | 44.4 |
| 5-FU | 9.7* | 2.1* | 4.6 | 7.2* | — | 0.62* | — | 11.6 |
| Ara-C | 0.076* | 0.054* | 1.4 | 0.22* | — | 0.035* | — | 6.3 |
| CDDP | 0.37 | 0.27 | 1.4 | 0.32 | — | 0.13 | — | 2.5 |
| MTX | 0.014 | 0.017 | 0.8 | 0.0078 | — | <0.0025 | — | >3.12 |
| MMC | 0.02 | 0.01 | 2.0 | 0.057 | — | 0.011 | — | 5.20 |
| ACNU | 7.60 | 5.40 | 1.4 | 10.0 | — | 3.10 | — | 3.20 |
| Mitoxantrone | 0.019 | 0.0081 | 2.3 | 0.36 | 0.074 | — | — | 4.9 |
| Etoposide | 0.27 | 0.098 | 2.8 | >20.0 | 7.4 | — | — | 2.7 |
| VCR | 0.0271 | 0.00325 | 8.3 | 0.730 | 0.0351 | — | — | 20.8 |
| BLM | 2.1 | 0.01 | 202 | 0.56 | 0.0385 | — | — | 14.5 |
| PEP | 1.95 | 0.0165 | 118 | 0.48 | 0.0157 | — | — | 30.5 |

*μM
($IC_{50}$: μg/ml)

TABLE 7

| | Cell line | | | | | |
|---|---|---|---|---|---|---|
| | PLC/S (parent cells) | | | PLC/Col (resistant cells) | | |
| Anti-cancer agent | Anti-cancer agent alone | Compound (I) 5 μg/ml | Potentiation activity (times) | Anti-cancer agent alone | Compound (I) 5 μg/ml | Potentiation activity (times) |
| Compound (I) | 6.8 | — | — | 1.7 | — | — |
| ADM | 0.0050 | 0.0053 | 1.0 | 0.08 | 0.027 | 3.0 |
| PEP | 0.24 | 0.08 | 3.0 | 0.19 | 0.03 | 6.3 |

| | Cell line | | | | | |
|---|---|---|---|---|---|---|
| | PLC/S (parent cells) | | | PLC/ACR (resistant cells) | | |
| Anti-cancer agent | Anti-cancer agent alone | Compound (I) 20 μg/ml | Potentiation activity (times) | Anti-cancer agent alone | Compound (I) 20 μg/ml | Potentiation activity (times) |
| ADM | 0.048 | 0.016 | 3.0 | 0.06 | 0.18 | 3.7 |
| ACR | 0.019 | 0.017 | 1.0 | 0.07 | 0.043 | 1.8 |

($IC_{50}$: g/ml)

The foregoing results lead to the discovery that the malate of formula (I) well potentiates the activities of other anti-cancer agents as a result of combined use. Furthermore, the potentiation activity is excellent on tumor cells having resistance to the other anti-cancer agents.

A-IV: Tumor proliferation inhibiting activity

Procedure

Female BALB/c rats (7 weeks old), 8 per group, were used. Tumor cells (Meth-A) induced by methyl cholanthrene were transplanted intraperitoneally to the rats, and then the malate of formula (I) was administered intraperitoneally to the rats. The proliferation inhibiting activity of the malate was examined by comparing the weight of the tumor cells with that of the tumor cells in the non-treated control group.

The dose of the malate of formula (I) was 1.25, 2.5, 5.0, and 10.0 mg/kg/day. The administration schedule was as shown in Table 8 below. Mitomycin C (MMC) was administered as another anti-cancer agent. The weight of the tumor cells was measured, and the proliferation inhibiting activity was determined.

Results

The weight (g) of the tumor with respect to that of the tumor in the control group (T/C, %) after 16 days from the transplantation of the tumor cells, and the number of surviving rats after 16 days are shown in Table 8.

TABLE 8

| Drug[1] (dose) | Dosing schedule (day) | Tumor weight mean ± S.D. (g) | T/C (%) | Number of surviving animals (16 days later) |
|---|---|---|---|---|
| Control | — | 1.672 ± 0.530 | 100 | 8/8 |
| Compound (I) | | | | |
| (1.25) | 1, 3, 5 | 1.255 ± 0.533 | 75 | 8/8 |
| (2.5) | 1, 3, 5 | 1.327 ± 0.350 | 79 | 8/8 |
| (5.0) | 1 | 1.389 ± 0.644 | 83 | 8/8 |
| (10.0) | 1 | 1.091 ± 0.659 | 65 | 8/8 |
| MMC (1.0) | 1–5 | 0.347 ± 0.185 | 21 | 8/8 |

[1]Dose in mg/kg/day

The above results show that the malate of formula (I) significantly inhibited the proliferation Meth-A sarcoma cells in rats.

A-V: Anti-cancer activity potentiating action in vitro

Procedure

ICR nude mice (4-5 weeks old; 7 per group) were used. Human stomach cancer cell line H-81 was used as tumor cells. Tissue pieces, 2 mm in square, were taken, and transplanted subcutaneously to the right back portion of the nude mice. The volume of the tumor after transplantation was calculated by long diameter x short diameter x thickness x ½. Administration of a drug was started on the 11th day after the transplantation when the above tumor volume reached about 100 $mm^3$.

The sequence of the drug administration was as follows: A lipid emulsion of the malate of formula (I) (the lipid emulsion of Example 2) was intravenously administered, and 20±5 minutes later, adriamycin (ADM) was simultaneously administered intravenously. The administration was further repeated every five days from the day on which the administration was first carried out. The total number of administrations of each drug was four. The doses of the drugs in the individual groups are as shown in Table 9 below.

Results

The tumor volume of each mouse on the day of measurement was calculated by the long diameter x short diameter x thickness x ½, and the tumor proliferation inhibiting ratio to the control group to which no drug was administered was determined. The measurement was made on the days on which the drugs were administered, and four weeks after the start of drug administration. The results are shown in Table 9.

It will be understood in view of the foregoing that the lipid emulsion of this invention has a marked anti-cancer activity potentiating action.

A-VI: Anti-cancer activity potentiating action in vivo

Procedure

ICR nude mice, 6 per group, were used, and the experiment was conducted substantially in accordance with the procedure described in A-V.

As tumor cells, human tumor cells (muscle fibrosarcoma HT-1080) were used, and 5 days after the transplantation, drug administration was started.

The sequence of drug administrations was as follows: A lipid emulsion containing the malate of formula (I) (the lipid emulsion of Example 2) was intravenously administered, and 20±5 minutes later, adriamycin (ADM) was intravenously administered. The administration was further performed every 5 days from the day of starting the administration, and the total number of administrations was therefore 4.

Mitomycin C (MMC) was tested by the same way as above.

Results

The doses of the drugs in the individual groups are shown in Table 10-1.

Thirty-six days after the transplantation of the tumor, a tumor mass was extracted and its weight was measured. From the difference of the weight of the tumor from the non-treated control group, the tumor growth inhibition ratio (%) was calculated. The results are shown in Tables 10-1 and 10-2.

TABLE 9

| Drug | Dose (mg/kg) | Tumor growth inhibition rate (%) | | | | |
|---|---|---|---|---|---|---|
| | | 1st Starting day | 2nd 5 days later | 3rd 10 days later | 4th 15 days later | — 4 weeks later |
| Lipid emulsion | 10[(1)] | — | 15.7 | 18.9 | 17.1 | 14.4 |
| + | 2 | — | 16.5 | 45.7 | 49.5 | 45.2** |
| ADM | 5 | — | — | — | — | 59.7* |
| Lipid emulsion | 5[(1)] | — | | | | |
| + | | | 23.5 | 46.3 | 53.1 | 46.3** |
| ADM | 2 | — | | | | |
| Lipid emulsion | 10[(1)] | — | | | | |
| + | | | 24.3 | 49.9 | 57.6 | 53.3*** |
| ADM | 2 | — | | | | |
| Lipid emulsion | 5[(1)] | — | | | | |
| + | | | 33.3 | 83.4 | 88.0 | 84.5*** |
| ADM | 5 | — | | | | |

*$p < 0.5$,
**$p < 0.1$,
***$p < 0.01$
[(1)]Calculated as the malate of formula (I)
Note 1: With regard to ADM (5 mg/kg), the administration was carried singly, and the evaluation was made four weeks later.
Note 2: Assay was carried out on the significance from the control group only with regard to the results obtained four weeks later.

It is seen from the results given in Table 9 that the lipid emulsion containing the malate of formula (I), when used in combination with ADM, synergistically potentiates the activity of ADM. Particularly, the tumor volume showed a clear tendency to diminish in the group to which 5 mg/kg of the malate of formula (I) and 5 mg/kg of ADM were administered together. In any of the groups tested, no case of death was noted in the nude mice. Side-effects were neither observed.

TABLE 10-1

| Drug | Dose (mg/kg) | Day of administration | Tumor weight | Tumor growth inhibition ratio (%) |
|---|---|---|---|---|
| Control | — | — | 3.62 ± 1.78 | — |
| ADM | 4 | 5, 10, 15, 20 | 0.14 ± 0.32 | 96.1 |
| Lipid emulsion | 5[(1)] | 5, 10, 15, 20 | | |
| + | | | 0.03 ± 0.05 | 99.2 |
| ADM | 4 | 5, 10, 15, 20 | | |

[(1)]Calculated as the malate of formula (I)

TABLE 10-2

| Drug | Dose (mg/kg) | Day of administration | Tumor weight | Tumor growth inhibition ratio (%) |
|---|---|---|---|---|
| Control | — | — | 3.62 ± 1.78 | — |
| MMC | 3 | 5, 10, 15, 20 | 1.92 ± 0.27 | 47.0 |
| Lipid emulsion + MMC | 5[(1)] 3 | 5, 10, 15, 20 5, 10, 15, 20 | 0.56 ± 0.28 | 84.5 |

[(1)]Calculated as the malate of formula (I)

It is seen from the results given in these tables that the lipid emulsion of this invention significantly potentiated the activities of ADM and MMC against HT-1080.

The results of the foregoing pharmacological tests show that the malate of formula (I) in accordance with this invention has excellent anti-cancer activity and excellent activity of potentiating the activities of other anti-cancer agents, and that the lipid emulsion containing the malate of formula (I) has an excellent effect of potentiating the activities of other anti-cancer agents.

Now, a test for the stability of the lipid emulsion of this invention will be described.

[B] STABILITY TEST

The micro-emulsions containing the N-solanesyl-N,N,-bis(3,4-dimethoxybenzyl)ethylenediamine malate provided by this invention were tested for 3 months for stability. The content was measured by high-performance liquid chromatography (device: 655-15 made by Hitachi Limited), and the particle size distribution analyzer (CAPA-500, made by Horiba Limited). The results are shown in Table 11. In a stability test at room temperature (25° C.) for 3 months, almost no change was observed in content, appearance, pH and particle diameter. Accordingly, the micro-emulsion of this invention is very stable pharmaceutically.

TABLE 11

Stability Test

| Micro-emulsion | Test items | Immediately after preparation | 1 month | 3 months |
|---|---|---|---|---|
| Example 2 | Content (mg/ml) (residual rate, %) | 20.22 (100.0) | 20.26 (100.2) | 19.89 (98.4) |
| | Appearance | White non-transparent emulsion | — | — |
| | pH | 3.59 | 3.60 | 3.62 |
| | Mean particle diameter (μm) | 0.21 | 0.21 | 0.21 |
| Example 3 | Content (mg/ml) (residual rate, %) | 20.28 (100.0) | 20.36 (100.4) | 19.93 (98.3) |
| | Appearance | White non-transparent emulsion | — | — |
| | pH | 3.60 | 3.60 | 3.58 |
| | Mean particle diameter (μm) | 0.21 | 0.21 | 0.21 |
| Example 4 | Content (mg/ml) (residual rate, %) | 20.56 (100.0) | 20.52 (99.8) | 20.13 (97.9) |
| | Appearance | White non-transparent emulsion | — | — |
| | pH | 3.63 | 3.65 | 3.64 |
| | Mean particle diameter (μm) | 0.22 | 0.22 | 0.22 |
| Example 5 | Content (mg/ml) (residual rate, %) | 20.17 (100.0) | 20.15 (99.9) | 19.79 (98.1) |
| | Appearance | White non-transparent emulsion | — | — |
| | pH | 3.62 | 3.63 | 3.62 |
| | Mean particle diameter (μm) | 0.22 | 0.22 | 0.22 |
| Example 6 | Content (mg/ml) (residual rate, %) | 20.04 (100.0) | 20.04 (100.0) | 19.68 (98.2) |
| | Appearance | White non-transparent emulsion | — | — |
| | pH | 3.65 | 3.65 | 3.63 |
| | Mean particle diameter (μm) | 0.20 | 0.20 | 0.20 |

The invention will now be illustrated by the following examples showing the production of the compound of formula (I) and the lipid emulsion of the invention.

EXAMPLE 1

Production of N-solanesyl-N,N'-bis(3,4-dimethoxybenzyl)ethylenediamine malate of formula (I)

Twenty grams (0.02 mole) of N-solaneyl-N,N'-bis(3,4-dimethoxybenzyl)ethylenediamine was dissolved in 200 ml of ethanol, and a solution of 4.1 g (0.03 mole) of malic acid in 10 ml of ethanol was added, and the mixed solution was gently heated. Ethanol was then evaporated under reduced pressure. The residue was washed with ether, and recrystallized from a mixture of ethanol and ether to give 18.2 g (yield 78.7%) of the captioned malate as colorless crystals having a melting point of 42° to 44° C.

Acute toxicity test

Using mice, the malate of formula (I) obtained as above was tested for toxicity. It was found that in oral administration, no abnormality was found in the mice at a dose of 2,000 mg/kg. Toxicity was neither noted.

EXAMPLE 2

4.0 g of N-solanesyl-N,N'-bis(3,4-dimethoxybenzyl)ethylenediamine malate was added to 20 g of soybean oil described in the Japanese Pharmacopoeia, and the mixture was dissolved under heat. Then, 2.4 g of purified soybean phospholipid and 5 g of glycerol were added to the solution, and the mixture was vigorously stirred under heat. A suitable amount of distilled water was added, and the mixture was stirred by a polytron homogenizer to prepare a clude emulsion. The crude emulsion was emulsified under high pressure by a Gaulin high-energy type homogenizer, and distilled water was added to adjust the amount of the emulsion to 200 ml. There was obtained a micro-emulsion containing N-solanesyl-N,N'-bis(3,4-dimethoxybenzyl)ethylenediamine malate. The dispersed lipid particles had a mean particle diameter of 0.21 micron, and it did not contain particles having a size of at least 1 micron.

EXAMPLE 3

Example 2 was repeated except that 5 g of glycerol was used instead of 13 g of D-sorbitol. A micro-emulsion containing N-solanesyl-N,N'-bis(3,4-dimethoxybenzyl)ethylenediamine malate was obtained.

EXAMPLE 4

4.0 g of N-solanesyl-N,N'-bis(3,4-dimethoxybenzyl)ethylenediamine malate was added to 20 g of soybean oil described in the Japanese Pharmacopoeia, and the mixture was heated to form a solution. To the solution were added 2.4 g of purified yolk phospholipid and a suitable amount of distilled water. The mixture was stirred by a polytron homogenizer to prepare a crude emulsion. The crude emulsion was emulsified under high pressure by a Gaulin high-energy homogenizer, and distilled water was added to make 200 ml. A microemulsion containing N-solanesyl-N,N'-bis(3,4-dimethoxybenzyl)ethylenediamine malate was obtained. The dispersed lipid particles in the micro-emulsion had a mean diameter of 0.22 micron, and it did not contain particles having a size of at least 1 micron.

EXAMPLE 5

4.0 g of N-solanesyl-N,N'-bis(3,4-dimethoxybenzyl)ethylenediamine malate was added to 10 g of soybean oil described in the Japanese Pharmacopoeia and 10 g of MCT, and dissolved under heat. Purified soybean phospholipid (1.2 g), 1.2 g of purified yolk phospholipid and 5 g of glycerol were added, and the mixture was vigorously stirred under heat. After dissolving, a suitable amount of water was added, and the mixture was stirred by a polytron homogenizer to form a crude emulsion. The crude emulsion was emulsified under high pressure by a Gaulin high-energy homogenizer. Distilled water was added to make 200 ml. A micro-emulsion containing N-solanesyl-N,N'-bis(3,4-dimethoxybenzyl)ethylenediamine malate was obtained. The dispersed lipid particles in the micro-emulsion had a mean diameter of 0.22 micron, and it did not contain particles having a size of at least 1 micron.

EXAMPLE 6

Example 2 was repeated except that 20 g of soybean oil was used instead of 10 g of soybean oil. Thus, a micro-emulsion containing N-solanesyl-N,N'-bis(3,4-dimethoxybenzyl)ethylenediamine malate was obtained.

The dispersed lipid particles in the microemulsion had a mean particle diameter of 0.20 micron, and it did not contain particles having a size of at least 1 micron.

What is claimed is:

1. A intravenously injectable oil-in-water type microemulsion having an action of potentiating the activities of anti-cancer agents, said micro-emulsion comprising
    fine particles of a mean diameter of not more than 1 micron of a vegetable oil or a triglyceride of a medium-chain fatty acid having 8 to 12 carbon atoms containing 0.1 to 10% (w/v) of N-solanesyl-N,N'-bis(3,4-dimethoxybenzyl)ethylenediamine malate of formula (I) below,

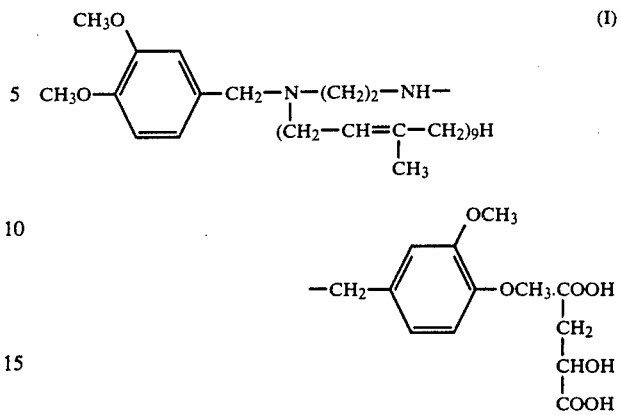

an aqueous medium, and
    0.05 to 25% (w/v) of physiologically acceptable phospholipid for dispersing said fine particles in said aqueous medium.

2. The micro-emulsion of claim 1 wherein the vegetable oil is pharmaceutically acceptable soybean oil.

3. The micro-emulsion of claim 1 wherein the physiologically acceptable phospholipid is a purified vegetable oil phospholipid.

4. The micro-emulsion of claim 3 wherein the purified vegetable oil phospholipid is purified soybean oil phospholipid.

5. The micro-emulsion of claim 1 which consists essentially of
    5 to 50% (w/v) of fine particles of a vegetable oil or a triglyceride of a medium-chain fatty acid having 8 to 12 carbon atoms containing 0.1 to 10% (w/v) of N-solanesyl-N,N'-bis(3,4-dimethoxybenzyl)ethylenediamine malate,
    0.05 to 25% (w/v) of physiologically acceptable phospholipid,
    an isotonizing agent selected from the group consisting of glycerol, sugar alcohols, monosaccharides, disaccharides and amino acids in an amount sufficient to isotonize the emulsion, and
    water.

6. The micro-emulsion of claim 1 which consists of
    5 to 30% (w/v) of fine particles of soybean oil having dissolved therein 0.3 to 3% (w/v) of N-solanesyl-N,N'-bis(3,4-dimethoxybenzyl)ethylenediamine malate,
    0.5 to 25% (w/v) of purified soybean oil phospholipid,
    1 to 5% (w/v) of glycerol, and
    the remainder being water.

7. The micro-emulsion of claim 1 wherein the fine particles of the oil have a mean particle diameter of not more than 0.3 micron.

8. The micro-emulsion of claim 4 wherein the purified soybean oil phospholipid has a phosphatidyl choline content of at least 80% by weight and an iodine value of 35 to 45.

* * * * *

UNITED STATES PATENT AND TRADEMARK OFFICE
CERTIFICATE OF CORRECTION

PATENT NO. : 5,004,756
DATED : April 2, 1991
INVENTOR(S) : OSAMU OGAWA, IKUO KISHI, YOSHIYUKI TAHARA, MASANORI SUGITA It is certified that error appears in the above-identified patent and that said Letters Patent is hereby corrected as shown below:

Col. 7, lines 3 and 4, delete "4-biphenylylaceticetic acid ester"

and insert therefor --N-solanesyl-N,N'-bis(3,4-dimethoxybenzyl)- ethylenediamine malate--.

Signed and Sealed this

Third Day of November, 1992

Attest:

DOUGLAS B. COMER

Attesting Officer

Acting Commissioner of Patents and Trademarks